United States Patent [19]

Winslow

[11] Patent Number: 5,466,648
[45] Date of Patent: Nov. 14, 1995

[54] SUPPORTED ALPHA-OLEFIN DIMERIZATION CATALYST

[75] Inventor: Linda N. Winslow, Cincinnati, Ohio

[73] Assignee: Quantum Chemical Corporation, Cincinnati, Ohio

[21] Appl. No.: 268,097

[22] Filed: Jun. 28, 1994

[51] Int. Cl.$^6$ .................................................. B01J 31/00
[52] U.S. Cl. ...................... 502/117; 502/102; 502/103; 502/118; 502/123; 502/159; 502/162; 502/169; 502/167; 502/171
[58] Field of Search .................................. 502/102, 103, 502/117, 118, 123, 159, 162, 169, 167, 171

[56] References Cited

U.S. PATENT DOCUMENTS 3,813,453  5/1974  Wideman .
3,897,512  6/1975  Brown et al. .
3,903,193  9/1975  Maly et al. .
3,940,346  2/1976  Luech .
5,059,739  10/1991  Hendriksen .
5,126,301  6/1992  Tsutsui et al. .......................... 502/117

*Primary Examiner*—Sharon Gibson
*Assistant Examiner*—E. D. Irzinski
*Attorney, Agent, or Firm*—William A. Heidrich

[57] ABSTRACT

The present invention is directed to a supported tungsten-based catalyst composition useful for the dimerization of alpha-olefins including ethylene. More particularly, the catalyst composition of the instant invention comprises an organic or inorganic support material that is contacted with a tungsten salt and an organic amine compound.

35 Claims, No Drawings

SUPPORTED ALPHA-OLEFIN DIMERIZATION CATALYST

FIELD OF THE INVENTION

The present invention is directed to a supported tungsten-based catalyst composition and to a catalyst system useful for the dimerization of alpha-olefins such as ethylene. More particularly, the tungsten-based catalyst composition of the instant invention comprises an organic or inorganic support material, a tungsten salt, an amine compound and, optionally, an organoaluminum compound. The catalyst system of the instant invention is formed by reacting the supported tungsten-based catalyst composition of the instant invention that does not contain an organo-aluminum compound as one of its components with at least one organoaluminum compound. It should be noted that when an organoaluminum compound is part of the solid catalyst composition, no organoaluminum cocatalyst is required to initiate dimerization of the alpha-olefin.

The present invention is further directed to a process for the dimerization of alpha-olefins using the aforementioned catalyst system of the instant invention. In accordance with the process of the instant invention one or more alpha olefins are dimerized under dimerization reaction conditions in the presence of the catalyst system of the present invention. In an alternative process, dimerization of an alpha-olefin is conducted in a fixed bed reactor in the presence of the solid catalyst composition which contains an organoaluminum compound as one of its components.

BACKGROUND OF THE INVENTION

Olefin dimerization and codimerization catalysts comprising a tungsten salt and an aniline compound are well known in the art. Moreover, various processes for dimerization or codimerization of ethylene using these unsupported catalysts are also well known and have been successfully developed in the prior art.

One such unsupported catalyst for dimerizing ethylene to 1-butene is disclosed in U.S. Pat. No. 3,813,453 to Wideman. More specifically, the unsupported tungsten catalyst disclosed in Wideman comprises a tungsten salt such as tungsten hexachloride or tungsten hexabromide and a nitrogen containing ligand of the formula:

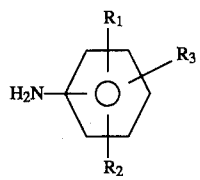

wherein $R_1$, $R_2$ and $R_3$ are selected from the group consisting of hydrogen and alkyl radicals containing from 1 to 4 carbon atoms. Suitable nitrogen containing ligands which are within the scope of the aforementioned formula include aniline, methylaniline, butylaniline, diethylaniline, trimethylaniline and the likes thereof. The unsupported tungsten catalyst is then activated by reacting it with a suitable organoaluminum compound, such as ethylaluminum dichloride or diisopropylaluminum chloride.

U.S. Pat. No. 3,897,512 to Brown et al. discloses another unsupported tungsten catalyst composition which is useful for the dimerization or codimerization of alpha-olefins. Specifically, the catalyst composition disclosed in Brown et al. comprises a tungsten salt selected from the group consisting of tungsten hexahalides and tungsten oxyhalides; a reducing agent having one of the following formulas: $R_nMX_{3-n}$ or $R_3M_2X_3$ wherein n is at least 1 but not more than 2, R is an alkyl radical containing from 1 to 10 carbon atoms, X is a halide, and M is a metal selected from the group consisting of boron, aluminum, gallium and indium; and a nitrogen containing ligand of the formula NR'R"R'" wherein R', R" are selected from the group consisting of hydrogen, alkyl, cycloalkyl, aryl, alkenyl and alkaryl; R'" is selected from the group consisting of hydrogen, alkyl, and alkenyl; and R', R" and R'" may contain from 1 to 20 carbon atoms when not hydrogen; and when R', R" and R'" are hydrocarbon, the hydrogen atoms attached to the carbon atoms may be mono- or polysubstituted by at least one member of the group selected from halogen, amino, nitro, cyano, alkoxy, carboxy and carboalkoxy; and two members of R', R" and R'" may be joined by carbon-carbon bonds to form a heterocyclic saturated ring. Representative compounds which encompass the formula NR'R"R'" include ammonia, n-butylamine, cyclohexylamine, aniline, N-methylaniline, 2,4,6-trimethylaniline and the likes thereof.

Similar unsupported tungsten-based catalysts as discussed hereinabove, which comprise a tungsten salt and a nitrogen containing compound such as aniline, are also disclosed in U.S. Pat. Nos. 3,903,193 to Maly et al. and 5,059,739 to Hendriksen.

Despite the current state of the art discussed hereinabove, none of those references disclose the supported tungsten-based catalyst composition of the present invention which has a far greater thermal stability as compared to the aforementioned unsupported tungsten-based catalysts. The superior thermal stability enables the supported catalyst composition of the instant invention to be successfully employed in reaction schemes that require or prefer high temperatures, such as commercially important fixed bed dimerization reactors.

SUMMARY OF THE INVENTION

This invention pertains to a highly active tungsten-based supported catalyst composition and to a catalyst system which is useful for catalyzing the dimerization of alpha-olefins. More particularly, the supported dimerization catalyst composition of the instant invention comprises an organic or inorganic support material, a tungsten salt, an amine compound having one of the formulas:

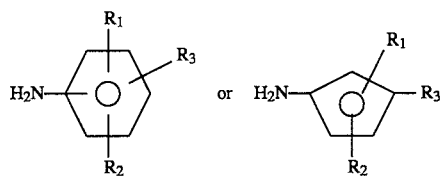

wherein $R_1$, $R_2$ and $R_3$ are the same or different and are selected from the group consisting of hydrogen and alkyls containing from 1 to 4 carbon atoms and, optionally, an organoaluminum compound.

The catalyst system of the instant invention comprises the aforementioned tungsten-based supported catalyst composition that does not contain an organoaluminum compound as one of its compounds and one or more organoaluminum compounds which are provided with the supported catalyst composition either before or during the dimerization process. It is emphasized that when the tungsten-based support catalyst composition contains, as one of its components, an organoaluminum compound, no organoaluminum cocatalyst is required to initiate dimerization. Such a supported catalyst composition is especially useful in fixed bed reactor processes.

The catalyst of the present invention represents a significant advancement in the art given the high catalytic activity which is observed for these supported catalysts and due to the high thermal stability of the supported tungsten-based catalyst compositions of the instant invention over the conventional unsupported tungsten-based catalysts. Moreover, the supported tungsten-based catalyst of the instant invention exhibits greater than 97% selectivity for the conversion of ethylene into 1-butene.

The support materials that are suitable in the present invention include organic supports such as polystyrene, modified polystyrene or styrene-divinylbenzene copolymer, and inorganic supports such as $SiO_2$, $Al_2O_3$, $TiO_2$, MgO, ZrO or mixtures thereof.

Suitable tungsten salts that are employed in the present invention include tungsten hexahalides such as tungsten hexachloride and tungsten hexabromide, and tungsten oxyhalides such as tungsten oxytetrachloride and tungsten oxytetrabromide.

Representative examples of the amine compounds having the aforementioned formulas employed in the present invention include aniline, methylaniline, dimethylaniline, trimethyl aniline, 2,6 dimethylaniline, dimethylaminoethylcyclopentadiene, dimethylaminocyclopentadiene, aminocyclopentadiene and the likes thereof.

The organoaluminum compounds employed in the instant invention as one of the components of the solid catalyst composition or to form the catalyst system, i.e. a cocatalyst, are characterized by one of the following formulas:

$$R_n AlX_{3-n}$$

or

$$R_3 Al_2 X_3$$

wherein n is an integer of 1 or 2, R is an alkyl radical containing from 1 to 6 carbon atoms, and X is a halide.

In another aspect of the present invention a process for dimerization of alpha-olefins, particularly ethylene, is disclosed. In this process, an alpha-olefin is dimerized under alpha-olefin dimerization reaction conditions in the presence of the catalyst system of the instant invention. In an alternative process of the instant invention, an alpha-olefin is dimerized under dimerization reaction conditions in the presence of a tungsten-based supported catalyst composition which contains as one of its components an organoaluminum compound. In accordance with this embodiment of the instant invention no cocatalyst compound is added to the reactor system during the dimerization process.

DETAILED DESCRIPTION OF THE INVENTION

In a preferred practice, the tungsten-based supported catalyst composition of the instant invention is prepared by initially contacting a support, which is either inorganic, such $Al_2O_3$, $SiO_2$, $TiO_2$, MgO, ZrO or mixtures thereof, or organic, such as polystyrene, modified polystyrene or styrene-divinylbenzene copolymer, or mixtures of such supports, with a tungsten salt and then adding a sufficient amount of an inert solvent to form a slurry. Thereafter, an amine compound is added to the slurry and reacted for a period of time sufficient to form the supported catalyst composition of the instant invention.

In an alternative practice of the instant invention, the catalyst composition is obtained by adding a reaction product of the amine compound and tungsten salt to the support.

In either of the above practices, the tungsten-based catalyst composition can be further treated with an organoaluminum compound and then dried to form a catalyst composition which may be used in a fixed bed dimerization reactor. Such a treated catalyst composition removes the necessity of adding a cocatalyst component during dimerization.

A preferred inorganic support employed in the present invention is silica that has a high surface area and high pore volume. The silica employed in the instant invention is preferably pure, however, it may contain minor amounts of the other aforementioned inorganic oxides. In general, the silica support is at least about 90 to about 95% by weight pure silica. In one preferred embodiment, the silica is at least 99% by weight pure silica.

The silica support, when utilized in the preparation of the supported tungsten-based catalyst composition of the instant invention, is preferably a high surface area, high pore volume material defined by a surface area between about 50 $m^2/gm$ and about 500 $m^2/gm$; a median particle size of about 20 microns to about 200 microns and a pore volume of about 0.5 cc/gm to about 3.0 cc/gm, as determined by standard B.E.T. measurement.

In a preferred practice the silica support is pretreated prior to its use to remove any impurities and/or reduce the number of surface hydroxyl groups present, which groups may inhibit the activity of the resultant catalyst composition.

To effectuate adequate reduction of hydroxyl groups from the surface of the silica support, the silica may be calcined in an inert atmosphere at a temperature of at least 150° C. Preferably, calcination of the silica is performed in a temperature range from about 150° to about 800° C. in an inert gas atmosphere, i.e. nitrogen or argon. Most preferably, the silica is calcined under a purge of nitrogen at a temperature of about 200° to about 600° C.

Another method of reducing the number of surface hydroxyl groups from the silica support involves contacting the silica with a hexaalkyl disilazane or a chlorosilane as disclosed for example in U.S. Pat. No. 4,530,913 to Pullukat et al., the contents of which are incorporated herein by reference. Of the hexaalkyl disilazanes useful in this application, hexamethyl disilazane, i.e., HMDS, is particularly preferred.

The silica may also be pretreated by combining the calcining method and treatment with a hexaalkyl disilazane. In this method, the sequence of pretreatment may be random; however, in the practice of this embodiment, it is preferred that the hexaalkyl disilazane treatment precede calcination.

When an organic support material is employed, it is preferred that polystyrene or a polystyrene/divinylbenzene copolymer be employed. The polystyrene/divinylbenzene copolymer employed in the instant invention may be unmodified or modified. If a modified polystyrene/divinylbenzene copolymer is employed, it is preferable that the modification occur via chloromethylation of the copolymer with chlorobenzene. Such a chloromethylation process is described in K. W. Pepper, et al., *J. Chem. Soc.*, 1953, 4097, the contents which are incorporated herein by reference.

In the practice of the present invention, the support material, e.g. the pretreated silica, is contacted with a tungsten salt and a sufficient amount of inert solvent such that a slurry is formed.

The tungsten salt contemplated by the instant invention is selected from the group consisting of tungsten hexahalides, such as tungsten hexachloride or tungsten hexabromide, and tungsten oxyhalides, such as tungsten oxytetrachloride or tungsten oxytetrabromide. Mixtures of such salts may also be utilized. Of these tungsten salts, it is preferred that the tungsten salt be tungsten hexachloride. It should be noted that, preferably, these tungsten salts should be substantially pure and substantially free from moisture.

The amount of tungsten salt contacted with the support can vary over a wide range depending on the type of support material employed. In the case of silica, the concentration of tungsten salt is from about 0.0010 to about 0.010 mole tungsten salt per gram of silica. More preferably, the concentration of tungsten salt is from about 0.0010 to about 0.0050 mole tungsten salt per gram of silica.

Preferred solvents employed in the instant invention to form the slurry include aromatic hydrocarbons and halogenated aromatic hydrocarbons, such as e.g. benzene, chlorobenzene and 1,2-dichlorobenzene. Of these solvents, it is particularly preferred that chlorobenzene be used.

Prior to use, it is preferred that the aromatic hydrocarbon or halogenated aromatic hydrocarbon solvents be treated to remove trace quantities of water, oxygen and other materials capable of adversely affecting the activity of the resultant catalyst. Conventional treatment methods, such as percolation through silica gel and/or the use of molecular sieves may be employed.

The amount of solvent employed in the present invention to form the slurry is preferably from about 10 to about 50 ml per gram of silica. More preferably, about 10 to about 20 ml of inert solvent per gram of silica is employed in the instant invention to form the slurry.

The slurry, comprising support material, tungsten salt and solvent, is heated at a temperature of about 20° to about 50° C. for a period of time between about 1 min to about 60 min. More preferably, the slurry is heated at a temperature of about 20° to about 40° C. for a period of time of about 1 min to about 5 min.

The aforementioned slurry mixture is then contacted with an amine compound. Specifically, the amine compound employed in the present invention has one of the following formulas:

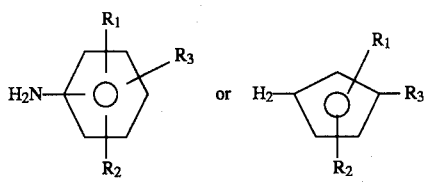

wherein $R_1$, $R_2$ and $R_3$ are the same or different and are selected from the group consisting of hydrogen and alkyls containing from 1 to 4 carbon atoms, preferably 1 to 2 carbon atoms. Exemplary amines having a cyclopentadiene ring include dimethylaminoethyl-cyclopentadiene, dimethylaminocyclopentadiene, aminocyclopentadiene and the likes thereof.

The preferred amine compound employed in the present invention is one which contains a phenyl ring. Exemplary amines which contain a phenyl ring include aniline; alkyl-substituted anilines such as methylaniline, ethylaniline and butylaniline; dialkyl-substituted anilines such as dimethylaniline and diethylaniline; and trialkyl-substituted anilines such as trimethylaniline and triethylaniline. When alkyl substituents are present, it is preferred that they be at the 2,3; 4,5 and/or positions of the phenyl ring. Preferably, the amine compound is 2,6-dimethyl aniline.

The molar ratio of amine compound to tungsten salt employed in the present invention is typically from about 0.5:1 to about 2.5:1. More preferably, the molar ratio of amine compound to tungsten salt is from about 1:1 to about 2:1. Most preferably, the molar ratio of organic amine compound to tungsten halide is about 2:1.

Typically, the contact of amine compound and the slurry of tungsten salt and support material occurs at a temperature range from about 20° to about 140° C. More preferably, contact occurs at a temperature range from about 80° to about 120° C. By preference, the resultant contact product of the support material, tungsten salt solvent and amine is continuously stirred under an inert gas atmosphere, e.g., nitrogen, for a period of time from about 0.1 hrs to about 2 hrs. Preferably, the contact occurs for a time period of about 0.1 hrs to about 1.5 hrs. Most preferably, this contact occurs for a time period of about 0.5 hrs to about 1.5 hrs.

Alternatively, the supported tungsten based catalyst of the present invention may be prepared by mixing the contact product of a tungsten salt and an amine compound as hereinbefore defined, with the support materials. Contact between the tungsten halide and amine compound is best carried out by admixing a solution of the amine compound and an inert solvent under an inert gas atmosphere, e.g., nitrogen or argon, to a heated or refluxed solution of the tungsten halide in a suitable solvent.

The contact between the amine compound and the tungsten salt usually occurs at a temperature in the range of between about 80° to about 140° C. More preferably, the aforementioned contact between the amine and tungsten salt occurs at a temperature range of between about 80° to about 120° C. This contact generally occurs over a period of time from about 0.1 hrs to about 2 hrs. Preferably, contact between the organic amine compound and the tungsten salt occurs at a time period of about 0.1 hrs to about 1.5 hrs; most preferably, about 0.5 hrs to about 1.5 hrs.

The resultant contact product comprising the tungsten halide and the amine compound is then admixed with the support material.

The concentration of the contact product comprising the tungsten salt and amine compound employed in the present invention is from about 0.00010 to about 0.010 mol per gram of silica. More preferably, the concentration of the contact product employed in the instant invention is from about 0.00010 to about 0.0010 mole per gram of silica.

This admixture comprising the support material and the contact product of an amine and tungsten salt is preferably heated at a temperature from about 20° to 80° C. More preferably, heating is at a temperature of about 20° to about 50° C. Admixing is preferably conducted for a period of time from about 0.1 hrs to about 3 hrs under an atmosphere of nitrogen with continuous stirring; more preferably, from about 1 hr to about 2 hrs.

The solid product that results from either of the above-defined methods is the catalyst composition of the present invention. Preferably, the solid product is isolated by removing the liquid phase by decantation, filtration, evaporation or the like. In a preferred embodiment the solid product is isolated by filtration and then by vacuum drying. Typically, the solid product representing the catalyst composition of the instant invention is dried in a vacuum for a period of time from about 2 hrs to about 24 hrs. More preferably, the solid catalyst composition is dried over a period of time from about 8 hrs to about 12 hrs.

In accordance with another embodiment of the instant invention, the solid product obtained above may be treated with an organoaluminum compound. In this embodiment, the solid product is reacted with an organic solvent (including those identified above, and aliphatic solvents such as heptane) in an amount sufficient to form a slurry of the solid product and thereafter an organoaluminum compound is added to the slurry.

Suitable organoaluminum compounds that can be employed to treat the supported tungsten-based catalyst of the instant invention are characterized by one of the following formulas:

$$R_nAlX_{3-n}$$

or $$R_3Al_2X_3$$

wherein n is an integer of 1 or 2, R is an alkyl radical containing from 1 to 6 carbon atoms, preferably 2 to 4 carbons and X is a halide. Mixtures of these organoaluminum compounds may also be utilized. Exemplary organoaluminum compounds which encompass these formulas are ethylaluminum dichloride, ethylaluminum dibromide, diisopropylaluminum chloride, diethylaluminum bromide, isobutylaluminum dichloride, ethylaluminum sesquibromide, ethylaluminum sesquichloride, butylaluminum dichloride, diisoamylalumminum chloride, dihexylaluminum bromide, dibutylaluminum chloride, diisobutylaluminum bromide, dihexylaluminum chloride and diethylaluminum chloride. Of these, diethylaluminum chloride is most particularly preferred.

The molar ratio of organoaluminum compound to supported tungsten-based catalyst composition employed in this treatment process is from about 1 to about 20. More preferably, the molar ratio of organoaluminum compound to supported tungsten-based catalyst composition employed in this treatment process is from about 2 to about 10.

This admixture comprising the solid catalyst composition, solvent and organoaluminum compound is reacted at a temperature from about 10° to about 80° C. Preferably, the above treatment with an organoaluminum compound is conducted at a temperature from about 20° to about 30° C. Treatment of the supported catalyst composition with an organoaluminum compound is preferably conducted for a period of time from about 1 min. to about 2 hrs; more preferably, from about 30 min. to about 1 hr.

The treated solid product that results is isolated by removing the liquid phase by any of the methods mentioned previously hereinabove. Furthermore, the solid product may be washed with a suitable solvent and then isolated as before. The organoaluminum treated catalyst composition is dried in a vacuum using the conditions mentioned previously herein.

The catalyst system of the instant invention which is not treated with an organoaluminum compound is then contacted with a suitable cocatalyst component. The catalyst system is formed by admixing the aforementioned solid catalyst composition with a suitable cocatalyst compound either before or during the dimerization of one or more alpha-olefins.

Suitable cocatalyst components include, for example, conventional organoaluminum compounds that are well known in the art. Preferably, the cocatalyst component employed in the instant invention is characterized by one of the following formulas:

$$R^4_nAlX^1_{3-n}$$

or $$R^4_3Al_2X^1_3$$

wherein n is an integer of 1 or 2, $R^4$ is an alkyl radical containing from 1 to 6 carbon atoms, preferably 2 to 4 carbons and $X^1$ is a halide. Mixtures of cocatalysts having these formulas may also be utilized. Exemplary cocatalyst components which encompass these formulas are ethylaluminum dichloride, ethylaluminum dibromide, diisopropylaluminum chloride, diethylaluminum bromide, isobutylaluminum dichloride, ethylaluminum sesquibromide, ethylaluminum sesquichloride, butylaluminum dichloride, diisoamylaluminum chloride, dihexylaluminum bromide, dibutylaluminum chloride, diisobutylaluminum bromide, dihexylaluminum chloride and diethylaluminum chloride. Of these, diethylaluminum chloride is most particularly preferred.

The molar ratio of cocatalyst component to supported tungsten-based catalyst composition depends upon the type of dimerization being contemplated. Typically, the concentration, expressed in molar ratio of cocatalyst component to catalyst composition, is from about 1 to about 200. More preferably, the molar ratio of cocatalyst component to catalyst composition is from about 1 to about 100.

In still another aspect of the present invention a process for dimerizing one or more alpha-olefins is set forth. This process comprises dimerizing one or more alpha-olefins in the presence of the catalyst system of the instant invention. When the solid catalyst composition contains an organoaluminum compound as one of its components, dimerization of an alpha-olefin can be conducted without the addition of any cocatalyst component.

Alpha-olefins contemplated in this regard include alpha-olefins containing from two to twelve carbon atoms such as ethylene, propylene, butene, pentene and the like. In a particularly preferred embodiment, the alpha-olefin is ethylene.

In either process of the instant invention, dimerization occurs preferably at a temperature in the range of between about 20° to about 120° C. More preferably, the temperature is in a range from about 20° to about 100° C. Dimerization further preferably occurs at a pressure in the range from about 30 to about 1000 psig, more preferably, between about 200 to about 600 psig. In a particularly preferred embodiment, ethylene dimerization occurs in the presence of a solvent, such as toluene or isobutane.

It is noted that the catalyst of the instant invention shows very high selectivity, in the range of about 98.5 to about 99%, for e.g. producing 1-butene from ethylene. Moreover, the catalyst of the instant invention is more thermally robust than prior art catalysts as briefly described hereinbefore. By thermally robust, it is meant that the supported tungsten-based catalyst of the instant invention is able to dimerize one or more alpha-olefins at temperatures greater than 60° C. without any significant diminishment of catalytic activity.

The following examples are given to illustrate the scope of the present invention. Because these examples are given for illustrative purposes only, the invention embodied therein should not be limited thereto.

EXAMPLE 1

Preparation of Support Tungsten-Based Catalyst Composition

A supported tungsten-based catalyst composition was prepared in accordance with the preferred process of the instant invention. Specifically, the supported tungsten-based catalyst composition of this example was prepared as follows:

Into a 250 ml, four-necked round bottom flask, purged with nitrogen gas free of oxygen and moisture, was placed 1.015 grams of dried Davison 948 silica and 0.400 grams of tungsten hexachloride, $WCl_6$. The dried silica was prepared by heating the silica, under nitrogen, at 600° C. for 6 hrs. The silica utilized in this example was characterized by standard B.E.T. method as having a surface area of about 220 $m^2/gm$, a median particle size of about 45 microns, and a pore volume of about 1.26 cc/gm.

To the flask containing the pretreated silica and $WCl_6$, was added 20 ml of chlorobenzene to form a slurry. This slurry was then stirred for about 2.25 hours at room temperature. Thereafter, 0.248 ml of 2,6 dimethylaniline (2.0 equivalents per tungsten) was added dropwise to the slurry.

This mixture was then heated to 90° C. for about 1.5 hours. During this period, an orange-brown solid material formed in the flask. The orange-brown solid was collected by vacuum filtration and dried for about 16 hours under vacuum. The solid catalyst thus recovered was found to contain 9.89% W, by weight, as analyzed by Inductively Coupled Plasma (ICP).

Dimerization of Ethylene

The solid catalyst composition obtained above was then utilized in the dimerization of ethylene. That is, a 2-1 Autoclave Engineers (Trademark) reactor was charged with 0.233 grams of the above solid catalyst composition. Thereafter, 100 ml of dried toluene or isobutane, which was prepared by passing it through 4Å molecular sieves, was flushed into the reactor.

Diethylaluminum chloride (DEAC) (4.5 ml; 1.59M in heptane) was then added to the reactor via a syringe. Another 100 ml of dried toluene or isobutane was used to flush the cocatalyst into the reactor and 100 psig of dry nitrogen was also added.

Ethylene was then introduced into the reactor and the pressure inside the reactor was maintained at 400 psig. The reaction temperature was 40° C. and ethylene was fed on demand with continuous stirring.

The dimerization data for this reaction is summarized in Table I. As shown therein the activity of the catalyst, which is expressed in all of the following examples as gm ethylene consumed/gm tungsten.hr, was 5440.

Direct GC analysis of the gas mixture indicated that the product mixture was composed of 98.9% 1-butene, 0.67% 2-ethyl-1-butene and 0.48% 3-methyl-1-pentene. The chemical composition was determined on a Varian 3700 Gas Chromotograph, equipped with a 4'×0.125" chromosorb 102 80/100 mesh column.

EXAMPLE 2

A solid catalyst composition was made in accordance with the procedure of Example 1 except that 0.213 gms of $WCl_6$, 2.04 g silica, and 0.132 mL 2,6-dimethylaniline were employed in its preparation. This resulted in a solid catalyst composition which contained 3.89% W.

The dimerization reaction using 0.216 gms of the catalyst composition having this lower loading of W was conducted in the manner set forth in Example 1.

The dimerization data for this example is shown in Table I. As shown therein, the catalyst composition prepared with the lower W loading exhibited higher activity (6530 gm ethylene consumed/gm tungsten.hr). This activity enhancement is believed to be due to the higher dispersal of active catalyst sites on the lower loaded catalyst.

EXAMPLE 3

A solid catalyst composition was prepared in accordance with the procedure of Example 1 except that the silica was pretreated at 200° C. instead of 600° C. and 0.25 gm of $WCl_6$, 2.02 g silica, and 0.155 mL 2,6-dimethyaniline were used. The solid catalyst composition of this example contained 4.12% W.

Ethylene dimerization using 0.412 gms of the above-identified solid catalyst was conducted in the manner set forth in Example 1.

The data for this reaction is shown in Table I. Specifically, the catalyst activity using the above catalyst composition was determined to be 5190 gm ethylene consumed/gm tungsten.hr. This catalyst was less active than the preceding catalysts using silica which was calcined at 600° C. This reduction in catalytic activity is believed to be caused by a more uniform active site distribution which is produced using the 600° C. dried silica then the 200° C. dried silica.

EXAMPLE 4

A solid catalyst composition was prepared in accordance with the procedure outlined in Example 3 except that 0.207 gms of $WCl_6$, 2.02 g silica, and 0.13 mL 2,6-dimethylaniline were employed. This lower amount of $WCl_6$ resulted in a solid catalyst composition which contained 3.49% W. The dimerization reaction was conducted in accordance with the procedure of Example 1.

The dimerization data for this solid catalyst composition is shown in Table I. As shown therein, the catalyst composition had an activity of 3210 gm ethylene consumed/gm tungsten.hr. The activity of this catalyst composition is lower than the catalyst composition of Example 3 which contained a higher loading of W. This decrease in activity is believed to be caused by a lower dispersal of active catalyst sites on the lower loaded catalyst composition.

EXAMPLE 5

A solid catalyst composition was prepared in accordance with the procedure of Example 1 except that the silica was dried at 200° C. and 0.204 gms of $WCl_6$, 1.02 g silica, and 0.127 M1 2,6-dimethylaniline were added to the silica. Additionally, instead of heating the final mixture at 90° C. as in Example 1 the mixture was stirred under $N_2$ at room temperature for 18 hrs. The catalyst composition contained 5.65% W.

The dimerization reaction was conducted using the procedure of Example 1. The dimerization data for this catalyst composition is shown in Table I. The catalytic activity for this catalyst composition was 5190 gm ethylene consumed/gm tungsten.hr.

EXAMPLE 6

A catalyst composition was prepared using the alternate method of the instant invention. In accordance with this alternative method as described hereinbefore, an unsupported catalyst composition is first formed and then contacted with Davison 948 silica which has been dried at 200° C.

In accordance with this method, 5.045 gms of $WCl_6$, 3.14 ml of 2,6-dimethylaniline and 50 ml of chlorobenzene were initially reacted together at a temperature of about 120° C. This mixture was stirred under nitrogen for a period of about 1 hr to form an orange-brown precipitate. The liquid phase was removed by filtration and the resultant solid product, representing the unsupported catalyst composition, was dried under vacuum for about 16 hrs.

To 0.10 gms of the unsupported catalyst composition, was added 1.00 gms of 200° C. dried Davison 948 silica and 20 ml of chlorobenzene. The thus formed mixture was stirred at 25° C. for a period of about 2 hrs under a nitrogen gas flow. Thereafter, the liquid phase was removed by filtration. The remaining solid phase, representing the supported catalyst composition was then dried under vacuum for 16 hrs. The catalyst composition contained 2.20% W.

Ethylene dimerization using the above catalyst composition was conducted in accordance with the procedure of Example 1. The activity of the resultant catalyst composition, which is shown in Table I, was determined to be 2640 gm ethylene consumed/gm tungsten.hr. Although the activity is lower than the catalyst composition of any of the preceding examples, the catalyst composition still showed a 98.3% selectivity for 1-butene.

Comparative Example 1

An unsupported catalyst composition was prepared in accordance with Example 4 except that 5.045 g $WCl_6$ and 3.14 mL 2,6-dimethylaniline were used and no silica was employed to support the catalyst. The unsupported catalyst contained 30.03% W. The dimerization reaction using the above unsupported catalyst was conducted in the manner as set forth in Example 1. The activity, which is shown in Table I, using the above unsupported catalyst was determined to be 3910 gm ethylene consumed/gm tungsten.hr.

EXAMPLE 7

A solid catalyst composition containing a chloromethylated polystyrene support was prepared as follows.

Into a 250 ml, four necked round bottom flask, purged with nitrogen gas free of oxygen and moisture, was placed 2.04 gms of polystyrene ("Bio-Beads S-X1" Biorad Chloromethylated Polystyrene) 200–400 mesh. The polystyrene was swelled with 20 ml of chlorobenzene for 16 hrs. This swelling is theorized to open the pore structure to accommodate a 14,000 Dalton molecular weight exclusion limit. After the 16 hr time period, the supernatent liquid was removed and the support was washed with 40 ml of chlorobenzene.

Into a separate vessel was added 0.210 gms of $WCl_6$ which was dissolved in 20 ml of chlorobenzene. The above solution was added to the wet support and 0.130 ml of 2,6-dimethylaniline (2.0 equivalents per W) was added dropwise. This mixture was then heated to 90° C. for 1 hr. During this time period a yellow solid formed in the flask. This yellow solid was collected by vacuum filtration and dried for 16 hrs under vacuum. The solid catalyst composition was found to contain 2.26% W by weight, as analyzed by ICP.

Dimerization of ethylene was conducted with this catalyst composition using the procedure of Example 1. The results of this reaction are shown in Table I. As shown therein, this catalyst composition had an activity of 2350 gm ethylene consumed/gm tungsten.hr.

EXAMPLE 8

A solid catalyst composition was prepared in accordance with the procedure of example 7, however, the polystyrene support was not swelled prior to use. The surface area of the non-swelled support was 0.226 $m^2$/gm and the pore volume was 0.0019 ml/gm. Additionally, 0.22 gms of $WCl_6$, and 0,137 mL 2,6-dimethylaniline were employed instead of the 0,210 gms used in Example 7. The solid catalyst composition contained about 2.36% by weight W.

The dimerization reaction was conducted in accordance with Example 1 except that 0.435 gms of catalyst was charged into the reactor. The results of this dimerization reaction are shown in Table I. The catalyst composition had a catalytic activity of 1610 gm ethylene consumed/gm tungsten.hr.

EXAMPLE 9

Temperature Effect

This example studies the thermal stability of a supported tungsten-based catalyst of the instant invention and a conventional unsupported catalyst at dimerization temperatures of 40° C. and 80° C.

For this example, the supported tungsten-based catalyst of Example 2 was used and dimerization of ethylene was performed at 40° C. and 80° C. Likewise, the unsupported catalyst composition of Comparative Example 1 was used for dimerization of ethylene at 40° C. and 80° C.

The results of these experiments are shown in Table II. As shown therein, the supported tungsten-based catalyst of the instant invention had improved thermal stability compared to the unsupported catalyst: the supported tungsten-based catalyst of the present invention exhibited only a 12.6% decrease in activity at 80° C., compared to 40° C. In contrast, the activity of the unsupported catalyst was diminished by 45.2% at 80° C. Therefore, the supported tungsten-based catalyst is more thermally stable than its unsupported counterpart.

EXAMPLE 10

A solid catalyst composition was prepared in accordance with the procedure of Example 1 except that 2.1 g of the solid catalyst composition was contacted with 10 ml of heptane to form a slurry thereof and then treated with 7.9 mmol of diethylaluminum chloride (DEAC) prior to dimerization. This treatment of the catalyst composition with DEAC was conducted at room temperature for a period of 1 hr.

Thereafter, the DEAC treated solid catalyst composition was isolated from the liquid phase by heating the mixture to 95° C. under a nitrogen purge to remove the solvent.

This treated solid composition was then used as a solid catalyst for dimerizing ethylene in a reactor. The conditions employed in Example 1 for dimerizing ethylene were followed expected that no cocatalyst component was utilized. The results of this dimerization for this example is shown in

13

Table III. As shown therein, the activity for the DEAC treated catalyst composition was 122 gm ethylene consumed/gm catalyst.hr.

To illustrate that the above catalyst composition does not require any cocatalyst to activate it, 2 mmol of DEAC was added to the reactor during dimerization. The results of this study, which are shown in Table III, indicate that the addition of a cocatalyst did not increase the activity of the catalyst.

EXAMPLE 11

A DEAC treated tungsten-based catalyst composition was prepared in accordance with Example 10 except that 1.0 g of the solid catalyst and 3.8 mmol of DEAC were employed. Additionally, the solid catalyst component was washed twice using 20 ml of heptane in each wash and then dried prior to its use.

This treated catalyst composition was then used in accordance with the procedure of Example 10. The dimerization results for this catalyst is shown in Table III. As shown therein, this catalyst composition has an activity of about 184 gm ethylene consumed/gm catalyst.hr.

To illustrate that the above catalyst composition does not require any cocatalyst to activate it, 2 mmol of DEAC was added to the reactor during dimerization. The results of this study, which are shown in Table III, indicate that the addition of a cocatalyst decreased the activity of the DEAC treated catalyst composition.

EXAMPLE 12

A DEAC treated tungsten-based catalyst composition was prepared in accordance with Example 10 except that 1.0 g of the solid catalyst and 7.9 mmol of DEAC were employed. Additionally, the solid catalyst component was washed twice using 20 ml of heptane in each wash and then dried prior to its use.

This treated catalyst composition was then used in accordance with the procedure of Example 10. The dimerization results for this catalyst is shown in Table III. As shown therein, this catalyst composition has an activity of about 288 gm ethylene consumed/gm catalyst.hr.

To illustrate that the above catalyst composition does not require any cocatalyst to activate it, 2 mmol of DEAC was added to the reactor during dimerization. The results of this study, which are shown in Table III, indicate that the addition of a cocatalyst decreased the activity of the DEAC treated catalyst composition.

Comparative Example 2

A catalyst composition was prepared in accordance with Example 10 except that it was not treated with DEAC.

This untreated catalyst composition was then utilized in accordance with the procedure of Example 10. Alternatively, a cocatalyst, 2 mmol of DEAC, was added to the reactor. The results using either of the two catalyst compositions is shown in Table III. The catalyst composition which did not contain any DEAC was less active than any of the catalyst compositions of Example 10–12.

TABLE I

| EXAMPLE | SUPPORT | % W | Catalyst Charge (gm) | ACTIVITY (gm C₂/gm tungsten · hr)* |
|---|---|---|---|---|
| 1 | 600° C. SiO$_2$ | 9.89 | 0.233 | 5440 |
| 2 | 600° C. SiO$_2$ | 3.89 | 0.216 | 6530 |
| 3 | 200° C. SiO$_2$ | 4.12 | 0.412 | 5190 |
| 4 | 200° C. SiO$_2$ | 3.49 | 0.267 | 3210 |
| 5 | 200° C. SiO$_2$ | 5.65 | 0.057 | 5190 |
| 6 | 200° C. SiO$_2$ | 2.20 | 0.137 | 2640 |
| 7 | Swelled Polystyrene | 2.26 | 0.415 | 2350 |
| 8 | Polystyrene | 2.36 | 0.435 | 1610 |
| CE1 | None | 30.03 | 0.078 | 3910 |

*Denotes activity of catalyst expressed in gm ethylene consumed/gm tungsten · hr under standard testing procedure 40° C., 400 psig.

TABLE II

| | TEMPERATURE EFFECT | |
|---|---|---|
| CATALYST | 40° C. ACTIVITY* | 80° C. ACTIVITY* |
| CE1 | 4000 | 2190 |
| 2 | 6270 | 5480 |

*Activity is expressed in gm ethylene consumed/gm tungsten · hr.

TABLE III

| EXAMPLE | % Al (ICP) | CATALYST CHARGE (gm) | ACTIVITY (gm C₂/gm catalyst · hr)* | COCAT |
|---|---|---|---|---|
| 10 | 5.28 | 0.223 | 122 | None |
|  |  | 0.216 | 118 | 2 mmol DEAC |
| 11 | 3.45 | 0.102 | 184 | None |
|  |  | 0.099 | 133 | 2 mmol DEAC |
| 12 | 3.45 | 0.099 | 288 | None |
|  |  | 0.102 | 225 | 2 mmol DEAC |
| CE2 | 0 | 0.196 | 104 | None |
|  |  | 0.196 | 293 | 2 mmol DEAC |

*Denotes activity of catalyst expressed in gm ethylene consumed/gm catalyst · hr under standard testing procedure, 40° C., 400 psig.

The above embodiments and examples are given to illustrate the scope and spirit of the instant invention. These embodiments and examples will make apparent to those skilled in the art other embodiments and examples. These other embodiments and examples are also within the scope of the instant invention. Therefore, the present invention should be limited only by the appended claims.

What is claimed is:

1. A supported tungsten-containing catalyst component useful for the dimerization of alpha-olefins comprising (a) an organic or inorganic support material; (b) a tungsten salt; and (c) an amine compound having one of the following formulas:

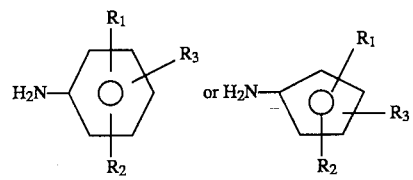

wherein $R_1$, $R_2$, and $R_3$ are the same or different and are selected from the group consisting of hydrogen and alkyls containing from 1 to 4 carbon atoms, and

represents a cyclopentadiene moiety having two double bonds.

2. The supported tungsten-containing catalyst component of claim 1 wherein the organic support material is selected from the group consisting of polystyrene, chloromethylated polystyrene, a polystyrene/divinylbenzene copolymer and a chloromethylated polystyrene/divinylbenzene copolymer.

3. The supported tungsten-containing catalyst component of claim 2 wherein said chloromethylated polystyrene or said chloromethylated polystyrene/divinylbenzene is chloromethylated with an organic solvent.

4. The supported tungsten-containing catalyst component of claim 3 wherein the organic solvent is chlorobenzene.

5. The supported tungsten-containing catalyst component of claim 1 wherein the inorganic support material is selected from the group consisting of $SiO_2$, $Al_2$, $MgO$, $TiO_2$, $ZrO$ and mixtures thereof.

6. The supported tungsten-containing catalyst component of claim 5 wherein the inorganic support material is $SiO_2$.

7. The supported tungsten-containing catalyst component of claim 6 wherein the $SiO_2$ is a calcined $SiO_2$.

8. The supported tungsten-containing catalyst component of claim 6 wherein the $SiO_2$ is a hexamethyl disilazane-treated silica.

9. The supported tungsten-containing catalyst component of claim 1 wherein the tungsten salt is selected from the group consisting of tungsten hexahalide and tungsten oxyhalide.

10. The supported tungsten-containing catalyst component of claim 9 wherein the tungsten hexahalide is tungsten hexachloride, tungsten hexabromide and mixtures thereof.

11. The supported tungsten-containing catalyst component of claim 9 wherein the tungsten oxyhalide is tungsten oxytetrachloride, tungsten oxytetrabromide and mixtures thereof.

12. The supported tungsten-containing catalyst component of claim 1 wherein the amine compound is selected from the group consisting of aniline, methylaniline, ethylaniline, butylaniline, dimethylaniline, diethylaniline, trimethylaniline, triethylaniline, dimethylaminoethylcyclopentadiene, dimethylaminocyclopentadiene and aminocyclopentadiene.

13. The supported tungsten-containing catalyst component of claim 1 wherein the amine compound has a phenyl ring which is substituted in the 2, 3; 4, 5 and/or 6 position.

14. The supported tungsten-containing catalyst component of claim 13 wherein the phenyl ring is substituted at the 2,6 position.

15. The supported tungsten-containing catalyst component of claim 14 wherein the amine compound is 2,6 dimethylaniline.

16. The supported tungsten-containing catalyst component of claim 6 wherein the concentration of tungsten salt is from about 0.0010 to about 0.010 mole per gram of silica.

17. The supported tungsten-containing catalyst component of claim 16 wherein the concentration of tungsten salt is from about 0.0010 to about 0.0050 mole per gram of silica.

18. The supported tungsten-containing catalyst component of claim 1 wherein the molar ratio of amine compound to tungsten salt is from about 0.5:1 to about 2.5:1.

19. The supported tungsten-containing catalyst component of claim 18 wherein the molar ratio of amine compound to tungsten salt is from about 1:1 to about 2:1.

20. The supported tungsten-containing catalyst component of claim 19 wherein the molar ratio of amine compound to tungsten salt is about 2:1.

21. The supported tungsten-containing catalyst component of claim 1 further comprising an organoaluminum compound.

22. The supported tungsten-containing catalyst component of claim 21 wherein the organoaluminum compound is characterized as having one of the following formulas:

$$R_nAlX_{3-n}$$

or $$R_3Al_2X_3$$

wherein n is an integer of 1 or 2, R is an alkyl containing from 1 to 6 carbon atoms, and X is a halide.

23. The supported tungsten-containing catalyst component of claim 22 wherein the organoaluminum compound is selected from the group consisting of ethylaluminum dichloride, ethylaluminum dibromide, diisopropylaluminum chloride, diethylaluminum bromide, isobutylaluminum dichloride, ethylaluminum sesquibromide, ethylaluminum sesguichloride, butylaluminum dichloride, diisoamylaluminum chloride, dihexylaluminum bromide, dibutylaluminum chloride, diisobutylaluminum bromide, dihexylaluminum chloride and diethylaluminum chloride, and mixtures thereof.

24. The supported tungsten-containing catalyst component of claim 22 wherein R is an alkyl radical containing from 2 to 4 carbon atoms.

25. The supported tungsten-containing catalyst component of claim 24 wherein the organoaluminum compound is diethylaluminum chloride.

26. The supported tungsten-containing catalyst component of claim 21 wherein the molar ratio of organoaluminum compound to supported tungsten-containing catalyst component is from about 1 to about 20.

27. The supported tungsten-containing catalyst component of claim 26 wherein the molar ratio of organoaluminum compound to supported tungsten-containing catalyst component is from about 2 to about 10.

28. A supported tungsten-containing catalyst component of claim 1 comprising (a) $SiO_2$ that has been calcined at about 600° C., (b) tungsten hexachloride and (c) 2,6-dimethylaniline.

29. A supported tungsten-containing catalyst system for use in the dimerization of alpha-olefins comprising (i) the supported tungsten-containing catalyst component of claim 1; and (ii) a cocatalyst component comprising at least one organoaluminum compound.

30. The catalyst system of claim 29 wherein the cocatalyst component has one of the following formulas:

$$R^4{}_n AlX^1{}_{3-n}$$

or $$R^4{}_3 Al_2 X^1{}_3$$

wherein n is an integer of 1 or 2, $R^4$ is an alkyl containing from 1 to 6 carbon atoms, and $X^1$ is halide.

31. The catalyst system of claim 30 wherein the cocatalyst component is selected from the group consisting of ethylaluminum dichloride, diethylaluminum dibromide, diisopropylaluminum chloride, diethylaluminum bromide, isobutylaluminum dichloride, ethylaluminum sesquibromide, ethylaluminum sesquichloride, dibutylaluminum chloride, diisoamylaluminum chloride, dihexylaluminum bromide, dibutylaluminum chloride, diisobutylaluminum bromide, dihexylaluminum chloride and diethylaluminum chloride, and mixtures thereof.

32. The catalyst system of claim 30 wherein $R^4$ is an alkyl radical containing from 2 to 4 carbon atoms.

33. The catalyst system of claim 32 wherein the cocatalyst component is diethylaluminum chloride.

34. The catalyst system of claim 30 wherein the molar ratio of cocatalyst component to the supported tungsten-containing catalyst component is from about 1 to about 200.

35. The catalyst system of claim 34 wherein the molar ratio of cocatalyst component to the supported tungsten-containing catalyst component is from about 1 to about 100.

* * * * *

UNITED STATES PATENT AND TRADEMARK OFFICE
CERTIFICATE OF CORRECTION

PATENT NO. : 5,466,648
DATED : November 14, 1995
INVENTOR(S) : Linda N. Winslow and Garry L. Fields It is certified that error appears in the above-indentified patent and that said Letters Patent is hereby corrected as shown below:

On the title page, add inventor to item [75] --Garry L. Fields-- and add --et al-- to item [19].

Signed and Sealed this

Twenty-fourth Day of September, 1996

Attest:

BRUCE LEHMAN

Attesting Officer

Commissioner of Patents and Trademarks